United States Patent [19]
Hell et al.

[11] Patent Number: 5,731,588
[45] Date of Patent: Mar. 24, 1998

[54] PROCESS AND DEVICE FOR OPTICALLY MEASURING A POINT ON A SAMPLE WITH HIGH LOCAL RESOLUTION

[76] Inventors: Stefan Hell, Nadlerstrasse 1, D-69117 Heidelberg, Germany, D-69117; Jan Wichmann, Blucherstrasse 3, D-69115 Heidelberg, Germany, D-69115

[21] Appl. No.: 682,793
[22] PCT Filed: Feb. 1, 1995
[86] PCT No.: PCT/DE95/00124
  § 371 Date: Nov. 21, 1996
  § 102(e) Date: Nov. 21, 1996
[87] PCT Pub. No.: WO95/21393
  PCT Pub. Date: Aug. 10, 1995

[30] Foreign Application Priority Data

Feb. 1, 1994 [DE] Germany .................. 44 03 027.4
May 11, 1994 [DE] Germany .................. 44 16 558.7

[51] Int. Cl.$^6$ .......................... G02B 21/00; G01N 21/64
[52] U.S. Cl. ............................. 250/458.1; 250/459.1
[58] Field of Search ............................. 250/458.1, 459.1, 250/461.1, 461.2, 484.4, 487.1

[56] References Cited

FOREIGN PATENT DOCUMENTS 3831880  5/1989  Germany .
WO9107651  5/1991  WIPO .

OTHER PUBLICATIONS

"Breaking the Diffraction Resolution Limit by Stimulated Emission: Stimulated-Emission-Depletion Fluorescence Microscopy", Stefan W. Hell, et al, Jun. 1, 1994, Optical Society of America, vol. 19, No. 11, pp. 780–782.

"Ground-State-Depletion Fluorescence Microscopy: A Concept for Breaking the Diffraction Resolution Limit", S.W. Hell, et al. 1995, Applied Physics B, pp. 495–497.

*Primary Examiner*—David P. Porta
*Assistant Examiner*—Richard Hanig
*Attorney, Agent, or Firm*—Weingarten, Schurgin, Gagnebin & Hayes LLP

[57] ABSTRACT

The invention relates to a device for the optical measurement of a point (7) on a sample (8) with high-local resolution, with a light source (1) to emit a beam (16) suitable for exciting an energy state in the sample (8), and a detector (9) to detect the emitted light. The lateral resolution of the device is improved in that there is a stimulation light beam (17) from the exciting light source (1) to generate stimulated emission at the point (7) on the sample (8) excited by the light beam (16), in which the exciting light beam (16) and the stimulation light beam (17) are arranged in such a way that their intensity distributions partly overlap in the focal region.

23 Claims, 2 Drawing Sheets

1

PROCESS AND DEVICE FOR OPTICALLY MEASURING A POINT ON A SAMPLE WITH HIGH LOCAL RESOLUTION

The invention concerns a device for optically measuring a point on a sample with high local resolution, with a light source to send out a exciting light beam suitable for exciting an energy state on the sample, a lens for focusing the exciting light beam on the points, the sample which can be arranged in the focal area of the lens, a separating device for separating out the emission light spontaneously emitted from the sample based on the excitation of the energy state and a detector for detecting the emission light.

The invention also concerns a process for optically measuring a point on a sample with high local resolution, in which an exciting light beam is focused on the point to be measured by means of a lens and excites the energy state there, and in which the emission light spontaneously emitted by the point, based on the excitation of the energy state, is separated out and detected.

FIELD OF THE INVENTION

The invention relates generally to an optical measurement device and more specifically to a device which performs optical measurements of a sample with high local resolution.

BACKGROUND

Such a device and such a process are known from practice. They have applications, for example, in microscopes, particularly raster microscopes. With a raster microscope, individual points on a sample are scanned and measured. In this way, the sample can be measured three-dimensionally. Luminescent, particularly fluorescent or phosphorescent samples, or samples with corresponding dyes, are used.

In such a device and such a process, it is desirable to achieve good local resolution. The local resolution is given by the spatial expansion of the so-called effective point-imaging function. This is a place-dependent function, which quantifies the probability with which a photon will be spontaneously emitted from a certain point in the focal range. It is identical to the spatial distribution of the probability that the energy state is excited at a certain point in the focal range. In conventional fluorescent microscopes,the effective point-imaging function of the lens at the wavelength of the excitation light, which gives the distribution of the intensity of the excitation light in the focal range of the lens and quantifies the probability with which an exposure photon will be met at a certain point in the focal range from a quantum-mechanics standpoint. In a raster microscope, the raster division is limited by the local resolution. With better local resolution, a finer division can therefore be selected, with which a better resolution of the reconstructed image can be achieved.

It is known that in a raster microscope, the resolution can be improved by having the light detected by the sample imaged on the point detector, which is arranged in one of the planes conjugated to the focal plane of the lens. Such an arrangement is called confocal. The better resolution is caused by the fact that two point-imaging functions determine the image in the confocal raster microscope: The effective point-imaging function and the detection-imaging function, which describes the image of the light to be detected that is emitted by the sample in the point detector and quantifies the probability with which a photo emitted from the focal range goes into the point detector from a quantum-mechanics standpoint. Since both exposure and detection must take place, the point-imaging function of a confocal raster microscope is the product of both probability distributions, i.e., from the effective point-imaging function and the detection-point-imaging function. This leads to a clearly narrower main maximum of the confocal point-imaging function compared to a microscope not arranged confocally. This corresponds to a higher resolution of the confocal microscope and brings about discrimination of all points that are not in the direct vicinity of the focus. The latter is the prerequisite for making three-dimensional images in the raster process.

SUMMARY

The task of the invention is to improve the generic device and the generic process in such a way that greater local resolution is achieved.

Regarding the device, this task is solved by the invention with a simulation light beam coming from the light source to produce stimulated emission of the sample excited by the exciting light beam in the point, wherein the exciting light beam and the stimulating light beam are arranged in such a way that their intensity distributions partially overlap in the focal range.

Regarding the process, the invention solves the task by having the sample excited by the exciting light beam in the point induced to simulated emission by a simulation light beam, wherein the intensity distributions of the exciting light beam and the stimulating light beam partially overlap in the focal range of the lens.

The stimulated emission induced by the stimulating light beam of the sample excited by the exciting light beam in the range covered by the intensity distributions of the excitation light and the stimulating light in the focal range of the lens make the excited energy state in the range covered calm down so it can no longer contribute to the spontaneously emitted radiation to be detected. The effective point-imaging function, which in the normal fluorescence microscope is identical to the point-image function of the lens at the wavelength of the excitation light, is thereby made narrower. This corresponds to increased spatial resolution. The improvement in the local resolution depends on the type of coverage of the intensity distributions. Both a lateral and an axial improvement in the local resolution can be achieved.

According to one version of the invention, it is advantageous if the sample is arranged on a positioning table, with which a mechanical raster movement can be carried out, at least in the direction of the optical axis. The device then corresponds to a raster microscope in which the sample can be scanned, at least along the optical axis. In this case, an improvement in local resolution in the axial direction is especially advantageous, since then better resolution can be achieved in that direction through finer rastering. Another advantage can be achieved if there is a beam-raster device for controlled scanning of the sample, with the exciting light beam and the stimulating light beam between the light source and the lens. The device is used as a raster microscope in which the sample can be scanned laterally or three-dimensionally. In such a raster microscope, better local resolution can also be achieved in the lateral direction by making the rastering smaller.

It is also advantageous if the stimulating light beam is moved laterally in the focal plane with regard to the exciting light beam. This arrangement makes the effective point-imaging function of the device narrower in the lateral direction. It can also be helpful if the stimulating light beam is moved along the optical axis in relation to the exciting light beam. This then improves the local resolution of the device in the axial direction.

Advantageously, there can also be at least one other stimulating light beam coming from the light source whose intensity distribution in the focal range of the lens is different from the intensity distribution of the other stimulating beams. In this arrangement, the intensity distributions of the additional stimulating beams also overlap the intensity distribution of the exciting light beam in the focal range of the lens, which again narrows the effective point-imaging function of the device. The type of narrowing of the effective point-imaging function can be chosen by the spatial arrangement of the stimulating light beams. Advantageously, the stimulating light beams can be spatially arranged symmetrically in relation to the exciting light beam. For example, the stimulating light beams can be arranged so that they run through a circular ring concentric to the exciting light beam. Here, the stimulating beams can be the same distance from one another. That way, the main maximum of the intensity distribution of the exciting light beam is narrowed evenly, so to speak, from several sides. Other arrangements of the stimulating light beams are also possible, and the precise choice of arrangement is left to the expert.

According to one advantageous version of the invention, the light source can include a laser, which emits portions of light of different wavelengths. The light of one wavelength is then used as the excitation light. The wavelength of the light is selected so that the energy status of the sample can thus be excited. The portion of light with the other wavelength is chosen for the stimulating light. The wavelength must be chosen so that the sample in the excited state can be calmed down via stimulated emission. Normally, the wavelengths necessary for the excitation light and the simulation light are different from one another. In the event that these wavelengths are the same, of course one can simply use a laser that only emits one wavelength.

It can also be advantageous if the light source includes at least two lasers, which emit light of different wavelengths. Then one laser is used to produce the excitation light and the other laser(s) to produce the stimulating light. Several stimulating light beams can be produced either with a laser, which is possible with a suitable filter or an appropriate array of mirrors, or several lasers can be used to produce one or more stimulating beams each. The use of lasers as a light source also has the advantage that light beams that can be highly localized spatially with high intensity are available.

More advantageously, a continuous-wave laser can be provided, which sends out excitation light. Using a continuous wave laser makes the arrangement less expensive. At least one laser can be provided that sends out a light pulse in a time sequence. More advantageously, a laser that sends out light pulses in a time sequence produces the stimulating light.

One advantageous arrangement consists of a continuous-wave laser to produce the excitation light and at least one laser that beams out light pulses in a time sequence to produce the stimulating light. The time within which the luminescence light should be detected by the detector is determined by the pulse length of the stimulating light. Here it is advantageous if the pulse length of the laser that emits the stimulating light is $10^{-10}$ to $10^{-5}$.

According to another advantageous arrangement, both the excitation light and the stimulating light are produced by lasers that emit light pulses in time sequence. In this case, the pulse length of the excitation light and the stimulating light should be smaller than the characteristic times for the spontaneous emission of the sample in the excited energy state. The pulse length of the stimulating light should be longer than the characteristic time for a dissociation process of the end state in which after the energy state is quieted down by stimulating emission, the sample is in a basic state that is even lower. From the latter, the sample is typically excited in the energy state. The pulse length of the excitation light is advantageously $10^{-15}$ to $10^{-9}$ s; the pulse length of the stimulating light is advantageously $10^{-12}$ to $10^{-9}$ s.

Advantageously, the laser can send out a light beam with a Gaussian intensity distribution to produce the stimulating light. That way, a Gaussian spatial intensity distribution is achieved in the focal plane as well. Such an intensity distribution has the advantage that it has no auxiliary maxima that could make the resolution worse. This is especially advantageous for the stimulating beams, since they can then be overlapped with the excitation beam so that they laterally overlap the main maximum of the intensity distribution of the excitation beam. In this case, any lateral maxima in the intensity distribution of the exciting light beam are eliminated because of the effect of the stimulating light beams in the effective point-imaging function. The stimulating light beams of the intensity distribution of the excitation beam can be overlapped from outside without any new auxiliary maximum being created in the effective point-imaging function. In this case, a clear narrowing of the main maximum of the effective point-imaging function is achieved without any auxiliary maxima occurring.

It is also favorable if the light source for producing the stimulated emission is high intensity, so that there is a nonlinear connection between that intensity and the occupation of the energy state of the sample. That way, with the stimulating light beam, the excited energy state in the range covered by the intensity distribution of the exciting and stimulating light can be quieted down by stimulated emission in a way that is very sharply limited spatially, so that the effective point-imaging function is also very sharply limited spatially, and at the same time a reduction in intensity of the overall luminescence is minimized.

According to one advantageous example of embodiment of the invention, the separating device has a time-control device, with which the detector can be turned on only directly after the pulse of the stimulating light dies. In this arrangement, if lasers that send out light pulses in a time sequence are used to produce both the excitation light and the separation light, the time-control device can also control the lasers in such a way that a simulation light pulse is emitted as soon as an excitation light pulse has died. The detector can then be activated with the same time-control device after the pulse of the stimulating light dies. The preferred pulse lengths of the laser were already mentioned above. A simple, clean separation of the emission light of the sample is possible even when the excitation light has the same wavelength as the emission light. The design of the device is mechanically simple, since no other filter elements have to be used.

According to another advantageous example of embodiment of the invention, the separation device can include a polarization element connected on the input side of the lens to polarize the stimulating light and a polarization element connected on the output side of the lens to polarize the light going to the detector with a conducting direction orthogonal to the polarization element connected to the lens on the input side. Connected on the input or output side here means both spatially and also in the direction in which the light runs before or after the lens. That way, it is possible to separate the emission light from the stimulating light reliably when the wavelengths are the same. A polarization element to polarize the excitation light can also be connected to the lens on the input side and another polarization element connected to the lens on the output side, which has a conducting direction orthogonal to the polarization element to polarize the light going to the detector. Thus, the light emitted by the sample can also be separated from the excitation light. It is also advantageous if the separation device has at least one wavelength filter. With the wavelength filter, the light emitted by the sample can be separated from the excitation light, if there are different wavelengths. A wavelength filter is connected to the lens on the output side. Color filters, dichroitic filters, monochromators, prisms, etc. can be used as wavelength filters. The separation device can also have a dichroitic mirror. The mirror is then arranged between the light source and the lens so that the light emitted from the sample is deflected by the dichroitic mirror, if it has a certain wavelength, and into the detector.

According to another advantageous version of the invention, the detector can be a point detector. A focusing element and a filter can be connected to the detector on the input side, wherein the filter is arranged in a plane optically conjugated to the focal plane of the lens.

The filter is, for example, an aperture, wherein its diameter is preferably so large that its image in the sample range is on the magnitude of the expansion of the effective point-imaging function at the wavelength of light to be detected. The point-imaging function of the device comes from the product of the effective point-imaging function and the detection-point-imaging function. Based on the point detector, an additional narrowing of the main maximum of the point-imaging function of the device and hence another improvement in resolution is thus achieved.

Another improvement in the local resolution of the device can be achieved by arranging a filter element permeable for the wavelength of the stimulating light between the light source and the lens that has an impermeable middle area and a permeable outer area for the wavelength of the excitation light. Such a filter element moves light from the main maximum into the bending auxiliary maxima in the intensity distribution of the excitation light in the focal range, wherein the main maximum is made clearly narrower. This leads to another narrowing of the effective point-imaging function. The increase in the intensity of the auxiliary maxima of the intensity distribution of the excitation light is, in this case, not disturbing, since they are suppressed because of the intensity distribution of the simulation light in the effective point-imaging function, since the intensity distributions partially overlap.

DESCRIPTION OF THE DRAWINGS

The invention will be described in greater detail below using the drawings.

DETAILED DESCRIPTION

Figure 1:
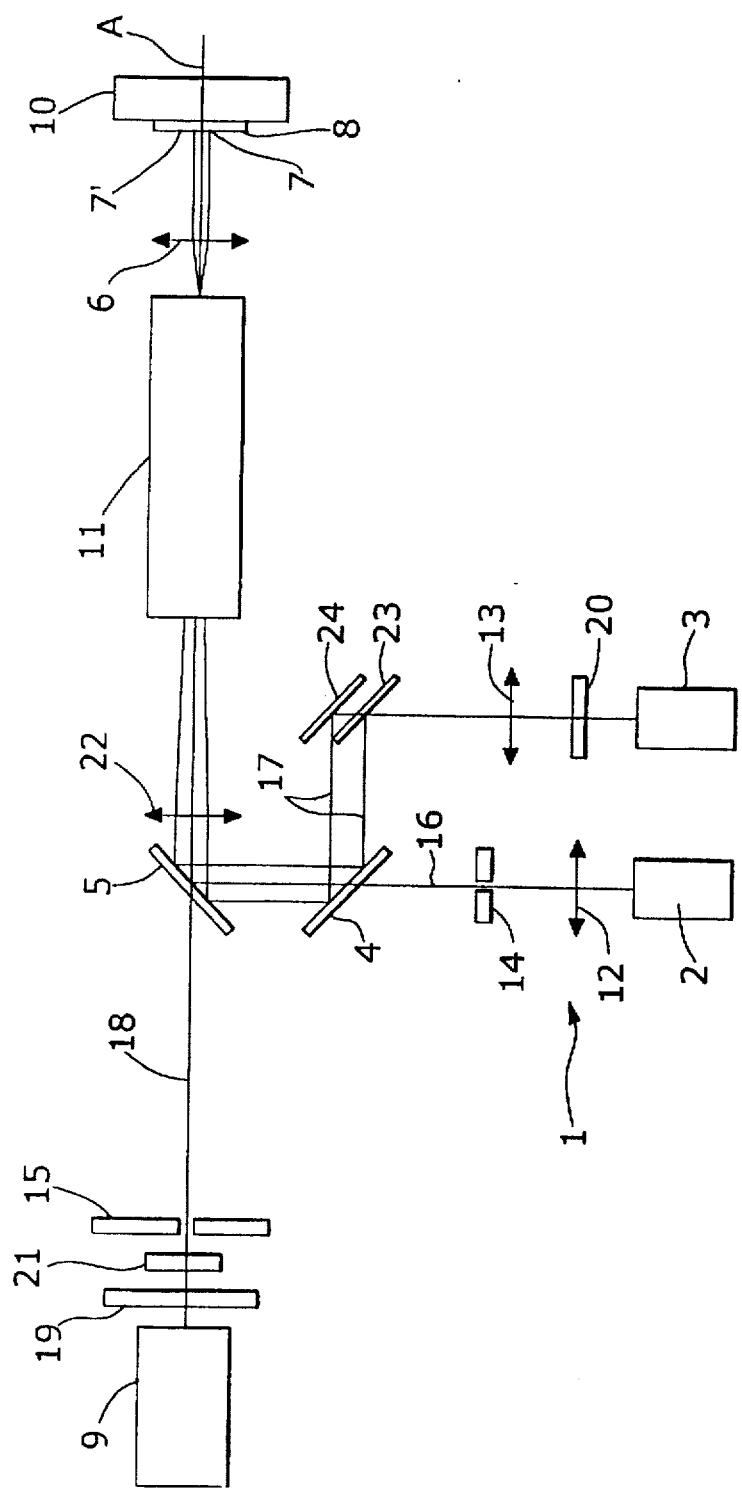
FIG. 1 shows a schematic drawing of one example of embodiment of the device in the invention.

FIG. 1 shows, the arrangement of a raster microscope as an example of embodiment of the device in the invention.

The raster microscope includes a light source 1 with a laser 2 to emit exciting light and a laser 3 to emit stimulating light. There are also dichroitic mirrors 4 and 5 and a lens 6, with which the exciting light and stimulating light coming from lasers 2 and 3 are deflected or focused on one point 7 of the sample 8. The point 7 has a local expansion which is an expansion of the surface here. A detector 9 is arranged to detect the emission light emitted by the sample 8 which is separated from the excitation light 18 with the dichroitic mirror 5. The sample is arranged on a positioning table 10. Between the light source 1 and the lens 6 is a beam-raster device 11 for controlled scanning of the sample 8 with the exciting light and the stimulating light. The light source 1 includes, in addition to the lasers 2 and 3, lenses 12 and 13 and a filter 14. With the lenses 12, the laser beam coming from the laser 2 is focused on the filter 14. The lens 13 is used to adjust the divergence of the exciting light beam and the stimulating light beams, so that they can be focused in the same plane using the lens 6. Apertures are usually used as filters. Behind the laser 3, there is a beam splitter 23 and a mirror 24 for dividing up the beam coming from the laser 3 into two stimulating light beams 17. The arrangement is selected so that the exciting light beam and the stimulating light beams meet on the mirror 4 in such a way that after deflection at the mirror 5 and passage through the lens 6, the intensity distributions of the beams partially overlap in the focal range of the lens 6.

In the example of embodiment shown, there are two stimulating light beams. However, one or more stimulating light beams may also be used. For this, either other lasers with beam paths similar to the beam path of the laser 3 can be used, wherein the beams are deflected in a suitable way to the mirror 4 and from there via the mirror 5 and the lens 6 to the point 7. But a laser 3 can also be used, as shown, and the stimulating light beam coming from the laser 3 can be broken into individual stimulating light beams using other beam splitters. It is important that the stimulating light beams all be arranged in such a way that their intensity distributions in the focal range of the lens 6 partially overlap with the intensity distribution of the exciting light beam. The laser 3 and the accompanying beam elements, not shown, such as beam splitters, lenses, etc. must be arranged so that the desired, predetermined arrangement of intensity distributions occurs in the focal range of the lens 6. For example, various stimulating light beams can be arranged on a circular ring through whose center point the exciting light beam 16 coming from the laser 2 runs.

In point 7, the energy state of the sample 8 is excited with the exciting light beam 16 that hits it there. The wavelength of the exciting light is chosen so it is suitable for exciting this energy state. Due to the impact of the stimulating light beam 17 coming from the laser 3, the energy state of the sample 8 excited with the exciting light is quieted via stimulated emission into a deeper state. For this, the laser 3 can emit the stimulating light as light pulses in a time sequence. The emission light spontaneously emitted by the sample 8 is deflected by the lens 6 and the mirror 5 into the detector 9 and detected there. In the drawing shown, the emission light is separated from the excitation light 16 by the dichroitic mirror 6 for detection in the detector 9. This is possible because as a rule the excitation light 16 has another wavelength than the emission light 18. For a further improvement in the selection of the emission light 18 based on its wavelength, a color filter 19 is arranged in front of the detector 9.

A polarizer 20 connected on the input side to the lens 6 to polarize the stimulating light 17 and a polarizer 21 connected on the output side to the lens 6 to polarize the light going to the detector are provided. The polarizers 20 and 21 have a conducting direction orthogonal to one another. With the polarizers 20 and 21, the emission light coming from the sample 6 can be separated from the stimulating light. The polarizers 20, 21 are necessary, since the stimulating light and the emission light have the same wavelengths and thus cannot be separated from one another by color filters. Moreover, an aperture 15 is connected on the input side to the color filter 19 and the polarizer 21, and it is in a plane optically conjugated to the focal plane of the lens. Alternately, the emission light coming from the sample can be separated from the stimulating light or the exciting light by a time-control device, not shown. This is possible when the laser 3 sends out stimulating light pulses in a time sequence and the laser 2 exciting light pulses in a time sequence. The time-control device must be turned on to the detector right after a pulse of the stimulating light dies. That way, the emission light can be separated from the stimulating light easily and reliably. The filter 19 and polarizers 20, 21 can be also arranged as shown in FIG. 1, if need be.

The beam raster device 11 is connected on the input side to a lens 22, with which the exciting light beam 16 and the stimulating light beams 17 are focused in the beam raster device 11. With the beam raster device 11, the exciting light beam 16 and the stimulating light beam 17 are controlled so that they scan the points 7, 7', ... of the sample 8 in a desired sequence. In each of the points 7, 7', the measurement described above is taken.

Figure 2:
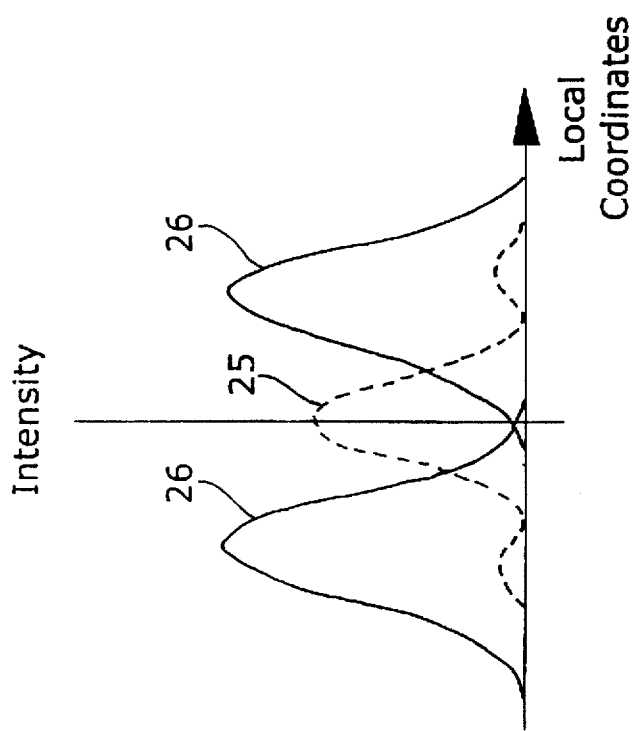

FIG. 2 shows the intensity distribution 25 of the exciting light beam and the intensity distributions 26 of two stimulating light beams 17. The intensity distribution 25 of the exciting light beam 16 has a main maximum and symmetrical auxiliary maxima in the lateral direction. The intensity distribution 26 of the stimulating beams 17 are Gaussian. The maxima of the Gauss distributions of the stimulating light are staggered laterally in relation to the maximum of the intensity distribution 25 of the excitation light. A symmetrical arrangement is chosen in which the two stimulating light beams are moved in the opposite direction at the same distance in relation to the central axis by the intensity distribution 25 of the exciting light. The intensity of the stimulating light is clearly greater than the intensity of the excitation light. The intensity of the stimulating light beam is chosen so that there is a nonlinear connection between that intensity and the occupation of the energy state of the sample.

Figure 3:
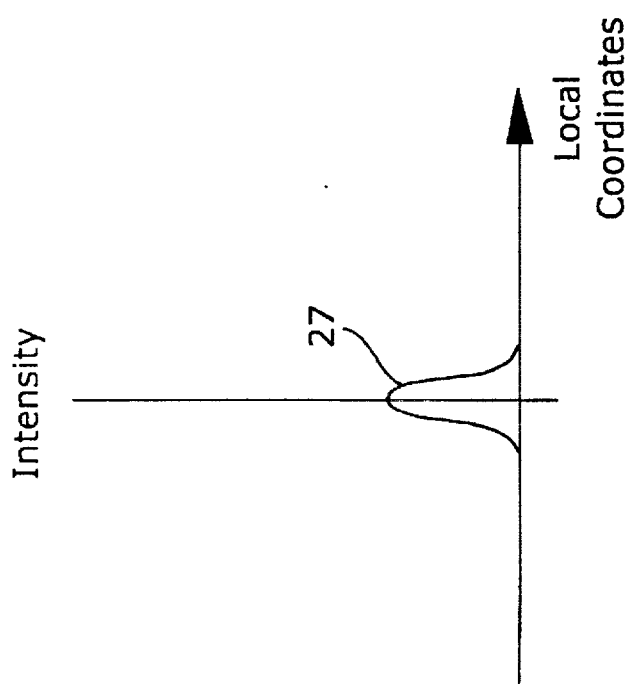
FIG. 2 shows an example of the intensity distribution of the excitation light and the intensity distributions of the stimulating light in the focal plane of the lens of the device in the invention and FIG. 3 shows the effective point-imaging function in the focal plane of the lens of the device in the invention.

FIG. 3 shows the effective point-imaging function in the focal plane of the lens, in which the intensity distributions in FIG. 2 go. The effective point-imaging function determines the local resolution of a raster microscope. As can be seen in the figure, the resulting effective point-imaging function has a maximum whose half-width value is clearly narrower than the half-width value of the intensity distribution of the exciting light, see FIG. 2. Also, through the overall effect of the intensity distributions shown in FIG. 2, the auxiliary maxima contained in the excitation light are eliminated. Because of the interaction of the exciting light beam and the stimulating light beams, one thus obtains an effective point-imaging function with a substantial improvement in lateral resolution, since both the half-width value of the effective point-imaging function is substantially reduced, and also the auxiliary maxima contained in the intensity distribution of the exciting light are eliminated, compared with the effective point-imaging function of a conventional fluorescence microscope, which is identical to the intensity distribution of the excitation light in the focal range of the lens. Because of the computational results, with the process in the invention, the lateral resolution of a raster microscope can be improved by a factor of roughly 5. The curves shown in FIGS. 2 and 3 show this in principle, but not to scale.

The process in the invention will be described below using FIG. 1. The sample 8 is put into a certain position on the optical axis A in the raster microscope shown with the positioning table 10. The lasers 2, 3 and the lenses 12, 13, the filter 14, the beam splitter 23 and the mirror 24 are arranged so that the stimulating light beams 17 and the exciting light beam 16 are deflected by the mirror 5 and the lens 6 to a selected sample point 7. The stimulating light beams 17 are aligned so that their intensity distributions overlap in the focal range of the lens 6 with the intensity distribution of the exciting light beam 16 in the way desired. The filter 19 and the polarizers 20, 21 are arranged so that the emission light emitted by the sample at the point 7 is separated from the exciting light and the separation light and is deflected into the detector 9 and detected there. After this measurement, a new point 7' is selected. For this, the exciting light beam 16 and the stimulating light beam 17 are deflected to the point 7'. There they are measured the same way as in point 7. After that, the exciting light beam 16 and the stimulating light beams 17 are deflected by the beam-raster device 11 to another point, until the sample 8 has been scanned and measured in the desired range in the lateral direction. Then the positioning table 10 is moved in the direction of the optical axis A. In that position of the sample 8, the whole measurement routine begins again. That way, the sample 8 can be scanned and measured three-dimensionally.

We claim:

1. A device for optically measuring a point of a sample with high local resolution comprising:

a light source to emit an exciting light beam suitable for exciting an energy state in the sample;

a lens for focusing the exciting light beam on the point of the sample that can be arranged in a focal range of the lens;

a separation device for separating out the emission light spontaneously emitted by the sample based on the excitation of the energy state; and a detector to detect the emission light, wherein a stimulating light beam coming from the light source to produce stimulated emission of the sample excited by the exciting light beam in the point of the sample, and wherein the exciting light beam and the stimulating light beam are arranged so that their intensity distributions partially overlap in the focal range.

2. The device according to claim 1 wherein the sample is arranged on a positioning table, with which a mechanical raster movement can be carried out at least in the direction of the optical axis (A).

3. The device according to claim 1 wherein between the light source and the lens, there is a beam-raster device for controlled scanning of the sample with the exciting light beam and the stimulating light beam.

4. The device according to claim 1 wherein the stimulating light beam is laterally staggered in relation to the exciting light beam in the focal plane.

5. The device according to claim 2 wherein the stimulating light beam is staggered along the optical axis in relation to the exciting light beam.

6. The device according to claim 1 wherein at least one other stimulating light beam coming from the light source is provided, whose intensity distribution in the focal range of the lens is different from the intensity distribution of the other stimulating light beams.

7. The device according to claim 6 wherein the stimulating light beam is spatially arranged symmetrically in relation to the exciting light beam.

8. The device according to claim 1 wherein the light source includes a laser that emits portions of light of different wavelengths.

9. The device according to claim 1 wherein the light source includes at least two lasers that emit light of different wavelengths.

10. The device according to claim 1 wherein at least one continuous-wave laser is provided that emits the exciting light.

11. The device according to claim 1 wherein at least one laser is provided that emits light pulses in a time sequence.

12. The device according to claim 11, wherein a laser, which emits light pulses in a time sequence, produces stimulating light.

13. The device according to claim 1 wherein the laser or producing the stimulating light emits a light beam with a Gaussian profile.

14. The device according to claim 1 wherein the light source for producing the stimulated emission is high intensity, so that there is a nonlinear connection between that intensity and the occupation of the energy state of the sample.

15. The device according to claim 1 wherein the separation device includes a time-control device, with which the detector can be turned on after a pulse of the stimulating light dies.

16. The device according to claim 1 wherein the separation device includes a first polarization element connected on the input side of the lens to polarize the stimulating light and a second polarization element connected on the output side of the lens to polarize the light going to the detector with a conducting direction orthogonal to the first polarization element connected to the input side of the lens.

17. The device according to claim 1 wherein the separation device has at least one wavelength filter.

18. The device according to claim 1 wherein the separating device has a dichroitic mirror.

19. The device according to claim 1 wherein the detector is a point detector, which is arranged in a plane optically conjugated to the focal plane of the lens.

20. The device according to claim 1 wherein a focusing element and a filter are connected to the detector on the input side, and wherein the filter is arranged in a plane optically conjugated to the focal plane of the lens.

21. The device according to claim 1 wherein between the light source and the lens there is a filter element that is permeable for wavelengths of the stimulating light, which has a nonpermeable central area and a permeable outer area for the wavelengths of the exciting light.

22. A method for optically measuring a point on a sample with high local resolution, in which an exciting light beam is focused on the point to be measured by means of a lens and there excites the energy state, and in which the emission light spontaneously emitted by the point based on the excitation of the energy state is separated out and detected, characterized by the fact that the sample excited by the exciting light beam into the point is induced by a stimulating light beam to stimulated emission, wherein intensity distributions of the exciting light beam and the stimulating light beam partially overlap in the focal range of the lens.

23. The method according to, claim 22 wherein the sample is scanned with the exciting light beam and the stimulating light beam.

* * * * *